United States Patent
Schapira et al.

Patent Number: 5,981,800
Date of Patent: Nov. 9, 1999

[54] PREPARATION PROCESS FOR 4-SUBSTITUTED DINITROANILINES

[75] Inventors: Joseph Schapira, Paris; Jean-Claude Cheminaud, Herblay; Jean-Jacques Gasse, Gaillon; Vincent Schanen, Paris; Benoît Rondot, Levallois Perret; Jean-Claude Lemoine, Chatenay Malabry, all of France

[73] Assignee: CFPI Agro, Gennevilliers, France

[21] Appl. No.: 09/056,266

[22] Filed: Apr. 7, 1998

[30]  Foreign Application Priority Data

Apr. 7, 1997 [FR] France ................................... 97 04236
Jul. 2, 1997 [FR] France ................................... 97 08360

[51] Int. Cl.$^6$ .................................................. C07C 209/18
[52] U.S. Cl. .............................................. 564/399; 564/87
[58] Field of Search ....................................... 564/87, 399

[56]  References Cited

U.S. PATENT DOCUMENTS

| | | | |
|---|---|---|---|
| 5,602,283 | 2/1997 | Sarel | 564/399 |
| 5,777,168 | 7/1998 | Kwiatkowski et al. | 564/399 |

FOREIGN PATENT DOCUMENTS

| | | | |
|---|---|---|---|
| 0 630 883 | 6/1994 | European Pat. Off. | |
| 2 069 755 | 11/1970 | France | |
| WO 97 01527 | 6/1996 | WIPO | |

*Primary Examiner*—Samuel Barts
*Attorney, Agent, or Firm*—Jones & Askew, LLP

[57]  ABSTRACT

Preparation process for 4-substituted dinitroanilines of formula

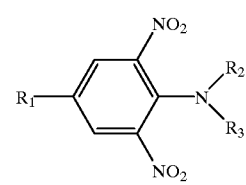

(I)

in which $R_1$ is chosen from the group containing the tert-butyl, sulphonamido, trifluoromethyl, methyl-sulphonyl and isopropyl radicals, $R_2$ and $R_3$, which are identical to or different from one another, represent a hydrogen atom, a linear or branched alkyl, cycloalkyl, haloalkyl or alkenyl radical containing less than 6 carbon atoms, characterized in that that it comprises successively:

a dinitration stage of the 4-substituted phenol corresponding to the sought 4-substituted dinitro-aniline, this dinitration stage being carried out in a reaction medium containing a slight excess of nitrating agent, a sufficient quantity of protons and a catalyst chosen from the group containing the soluble salts of the transition metals of columns IV to XII of the Periodic Table, preferably the soluble salts of $Fe_{III}$, $Fe_{II}$, $Zn_{II}$ and $Cu_{II}$ ions, an O-alkylation stage of the dinitrated 4-substituted phenol obtained in the preceding stage, by means of an alkylating agent, and an amination stage of the 4-substituted dinitrated phenoxy-ether obtained in the preceding stage by using a primary or secondary amine.

12 Claims, No Drawings

PREPARATION PROCESS FOR 4-SUBSTITUTED DINITROANILINES

The invention relates to a preparation process for 4-substituted dinitroanilines.

The dinitroanilines in question, which are known herbicides, act essentially as cell division inhibitors.

They are represented by the formula

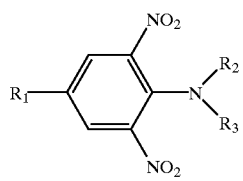
(I)

in which
R$_1$ is chosen from the group comprising the tert-butyl, sulphonamido, trifluoromethyl, methylsulphonyl and isopropyl radicals, R$_2$ and R$_3$, which are identical to or different from one another, represent a hydrogen atom, a linear or branched alkyl, cycloalkyl, halo-alkyl or alkenyl radical containing less than 6 carbon atoms.

Particularly useful dinitroanilines are butralin, trifluralin and oryzalin represented respectively by the formulae:

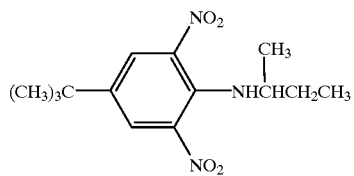
(II)

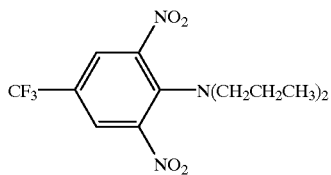
(III)

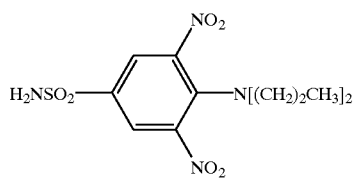
(IV)

It has already been proposed, in patent FR-A-7041719, to prepare butralin by proceeding successively:
- with the dinitration of 4-tert-butyl-phenol using nitric acid in an acetic medium,
- with the chlorination of the 2,6-dinitro-4-tert-butyl-phenol obtained in the preceding stage with the aid of thionyl chloride or phosphorus oxychloride in the presence of an amide such as formamide or dimethylformamide (DMF),
- with the condensation of the 4-tert-butyl-2,6-dinitrochlorobenzene formed in the preceding stage with two moles of sec-butylamine.

The dinitroaniline thus obtained must be recrystallized in an alcoholic medium.

Though this synthesis route is remarkable in its theoretical simplicity, owing to the limited number of intermediate stages, its implementation proves difficult, and purification of each of the intermediates is essential if a good-quality product is to be obtained.

Moreover, nitration leads to a nitroacetic effluent which is extremely difficult and expensive to treat and of course, even more so, to recycle in the process.

Furthermore, chlorination consumes excessive amounts of thionyl chloride and/or phosphorus oxychloride which are expensive products, making this method uncompetitive in economic terms.

Finally, there are risks of the formation of explosive derivatives during nitration.

Other known processes use alkylchlorobenzenes or alkylanilines as starting materials.

These known processes also have substantial drawbacks. Thus,
- the starting material consisting of alkyl-chlorobenzenes is not available commercially, so an additional chlorination stage is required and
- when the starting material is an alkylaniline, there is formation of N-nitrosamines in large quantities.

Therefore a particular aim of the invention is to overcome the drawbacks of the prior art and provide a preparation process for 4-substituted dinitroanilines which is better at meeting the various practical requirements that the existing methods.

Now, the Applicant has found, as a result of extensive research, that is aim can be achieved by implementing a process that is characterized in that it comprises, successively:

a dinitration stage of the 4-substituted phenol corresponding to the sought 4-substituted dinitroaniline, this dinitration stage being carried out in a reaction medium containing a slight excess of nitrating agent, a sufficient quantity of protons and a catalyst chosen from the group containing the soluble salts of the transition metals of columns IV to XII of the Periodic Table, preferably the soluble salts of Fe$_{III}$, Fe$_{II}$, Zn$_{II}$ and Cu$_{II}$ ions, an O-alkylation stage of the dinitrated 4-substituted phenol obtained in the preceding stage, by means of an alkylating agent chosen from the group containing, on the one hand, linear or branched alkyl mono-halides having at least 3 carbon atoms and which can include a saturated ring or at least one unsaturation, on the other hand, linear or branched alkyl polyhalides having at least 2 carbon atoms and which can include a saturated ring or at least one unsaturation, or yet again, the polyalkoxy-haloalkyl ethers represented by the formula (RO)$_n$R'X in which X represents a hydrogen, chlorine, bromine or iodine atom and R and R', independently of one another, represent a methyl, ethyl or propyl radical, n being such that the number of carbon atoms of the alkylating agent is $\geq 2$, in particular chloromethyl-polymethoxy ethers and chloromethyl-polyethoxy ethers, the oxides of ethylene and of propylene, and yet again, compounds with a structure corresponding to the formula

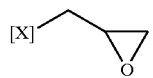

which represents epihalohydrins when X represents Cl or Br, glycidol when X represents OH, glycidyl ethers when X represents OR, R being an aliphatic chain with at most 12 carbon atoms, or an oxirane when X is an aliphatic chain R from 1 to 12 carbon atoms, an amination stage of the dinitrated 4-substituted phenoxy-ether obtained in the preceding stage by means of a primary or secondary amine.

According to an advantageous embodiment of the aforesaid process, the catalyst employed during the dinitration stage is chosen from the group containing ferric and ferrous chlorides, zinc and cupric chlorides, ferric, zincic and cupric nitrates as well as ferric, ferrous, zincic and cupric sulphates.

The proportion of catalyst relative to the phenol is from 1 to 50 per thousand, preferably from 5 to 30 per thousand.

The nitrating agent is chosen from the group containing nitric acid and water-soluble alkaline and alkaline-earth nitrates.

The excess of nitrating agent used for the dinitration stage is advantageously from about 10% to 30% by weight.

The quantity of protons which must be present in the nitrating medium is from 2 to 7, preferably from 2.4 to 6 and, even more preferably, from 2.6 to 2.9 equivalents relative to the phenol and can be provided by an acid called a co-acid and constituted by an inorganic acid chosen from the group containing hydrochloric, hydrobromic, sulphuric and phosphoric acids, or by an organic acid chosen from the group containing lower carboxylic acids, in particular acetic, propionic and oxalic acids.

The nitration stage can be carried out in a homogeneous nitric medium or in the presence of an inert solvent.

The inert solvent is chosen advantageously from the group containing aliphatic alkanes, especially hexane, heptane, octane, nonane and dodecane, chlorinated derivatives, especially dichloromethane, 1,2-dichloroethane, chloroform, trichloroethylene, tetrachloroethylene, and dialkyl-ethers, in particular diethyl- and dipropyl-ethers as well as dibutyl-ethers.

The reaction is advantageously carried out under atmospheric pressure and at temperatures from −20° C. to +80° C.

The 2,6-dinitrated derivative obtained can be separated and purified by standard techniques which are well known to a person skilled in the art.

When the nitration stage is carried out without solvent, the dinitrated derivative is precipitated by dilution and ice-cooling of the reaction medium, then separated by filtration.

Conversely, when the nitration stage is carried out in a solvent, the dinitrated derivative solubilized in the organic phase is isolated by decanting, the nitrating agent contained in the aqueous phase can then be recycled to the nitration stage once it has undergone concentration.

The purity of the 4-substituted 2,6-dinitrophenol derivative obtained is generally excellent and further purification is not required.

When the solvent is chosen judiciously, it does not become necessary to isolate the dinitrophenol and the solvent-containing solution can then be directly subjected to the following stage; this is the case for example when the solvent belongs to the family of halogenated solvents of the group containing methylene chlorides, 1,2-dichloroethane, 1,2-dibromoethane, chloropropane, isopropyl chloride, isopropyl bromide, butyl chlorides, 1,2-dichloropropane and 1,2-dibromopropane.

The yield for the dinitration stage is at least 92% and can reach 99%.

According to another advantageous embodiment of the process according to the invention, the alkylating agent used during the O-alkylation stage is either an alkyl monohalide represented by the formula $C_nH_{2n-1}X$ in which X is a chlorine, bromine or iodine atom and n is $\geq 3$, or an alkyl polyhalide represented by the formula $C_nH_{2n-m}X_{2+m}$ in which X is an atom of chlorine, bromine or iodine and $n \leq 2$ with $0 \leq m \leq 2n$.

The alkylating agent can be chosen from the group containing:

as alkyl monohalides, the n-propyl, isopropyl, n-butyl, sec-butyl, isobutyl, tert-butyl, n-pentyl, secamyl, 3-pentyl, neopentyl, hexyl, isohexyl, cyclohexyl, cyclopropyl, benzyl, allyl and polyalkoxyalkyl halides with a methoxy, ethoxy or propanoxy radical as the alkoxylated chain, as alkyl polyhalides, the dihaloethanes, in particular dichloroethane and dibromoethane, and dihalopropanes, in particular 1,2- and 1,3-dichloropropanes.

The reaction conditions of the etherification of the dinitrophenols are well known to a person skilled in the art.

In general, these reactions are carried out on the dinitrated phenol or on a corresponding alkaline phenate in aqueous medium or more advantageously in a biphasic medium by a phase transfer reaction.

The alkaline phenate can be a dinitrophenate either of sodium or of potassium, or of an organic salt such as ammonium, the quaternary tetra-alkyl ammoniums and the quaternary tetra-alkyl phosphoniums.

The alkylating agent, in solution in a solvent which is immiscible with water, is mixed with an aqueous solution of the alkaline phenate in the presence of a phase transfer catalyst which can be constituted by ammonium halide or a quaternary phosphonium salt.

The solvent can be chosen from the group containing aromatic solvents, aliphatic alkanes and ketones; preferably, it is chosen from the group containing toluene, O-xylene, m-xylene, p-xylene, hexane, heptane, octane, nonane, dodecane, methylethyl ketone, methylisobutyl ketone, cyclohexanone and mixtures of these solvents.

It is also possible for an excess of alkylating agent to be used as solvent.

The preferred catalysts are tetrabutylammonium chloride, tetrabutylammonium bromide, tetrabutylphosphonium bromide, triethylbenzylammonium chloride, trimethylbenzylammonium.

The alkylation reaction can be carried out at a temperature from 15° C. to 150° C., under atmospheric pressure or under a pressure of up to 15 bars.

The phase transfer reactions can be carried out at temperatures which vary from −10° C. to +50° C. and at atmospheric pressure whereas the reactions using lower alkyl halides can be carried out under a pressure of several tens of bars.

The dinitrated phenoxy-ether obtained at the end of this stage can be isolated from the reaction medium by techniques known to a person skilled in the art, such as extraction with a appropriate solvent or alternatively concentration followed by fractionation of the organic phase when the process employs a phase transfer reaction.

When an excess of alkylating agent is used as the solvent, the product is isolated by solubilization of the water-soluble salts, a second alkaline washing makes it possible to solubilize the unreacted dinitrophenate; back-extraction, in an acid medium, of the product resulting from this second washing then leads to a solution of dinitrophenol which can easily be recycled in a subsequent etherification operation.

The organic phase isolated after the second washing is subjected to evaporation of the excess of alkylating agent which can be re-used advantageously in the following operation.

However, when the solvent is chosen from the group containing toluene, xylene and aliphatic alkanes, especially heptane, octane, nonane, decane and dodecane, fractionation is not required and the organic solution obtained in this stage can be subjected to the amination stage directly.

According to another advantageous embodiment of the process according to the invention, the amination stage is carried out by reacting, under atmospheric pressure or under 3 to 5 atmospheres and at a temperature ranging from 30° C. to the reflux temperature of the medium, the product of the O-alkylation stage with an excess of secondary or primary amine chosen from the group containing amino-2-butane, N,N-diethylamine, N,N-dipropylamine, N-ethyl,N-butylamine, N-propyl-,N-methyl-cyclopropylamine, N-(2-chloroethyl),N-propylamine, N-propyl-,N-2-methyl-2-propenylamine, N-ethyl-,N-2-methyl-2-propenylamine in an inert solvent chosen from the group containing aromatic solvents and alcohols.

In a completely surprising fashion, the process according to the invention allows very high yields to be achieved, above 96%, without producing more than 1 ppm is of N-nitrosamines and without risk of formation of explosive products.

The successive stages of the process according to the invention are shown in the following reaction diagram:

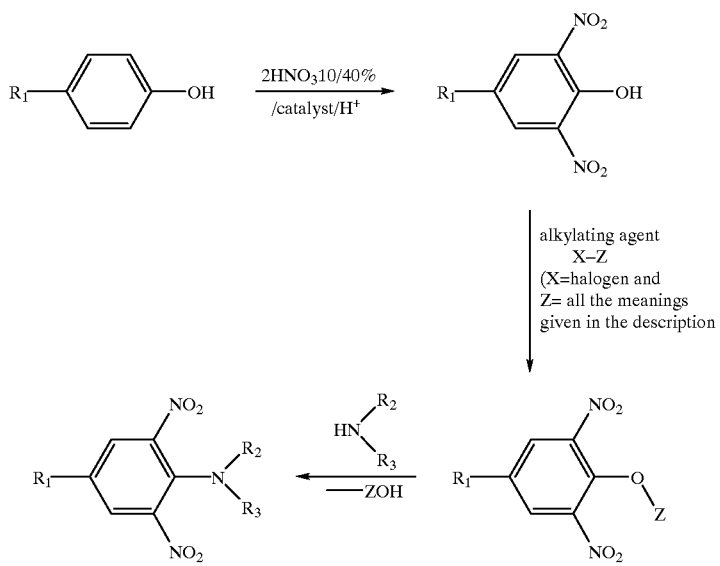

When the alkylating agent is polyfunctional, i.e. constituted for example by a dihaloethane, it is capable of reacting with two molecules of dinitrophenol and a polyetherification takes place, illustrated by the reaction diagram:

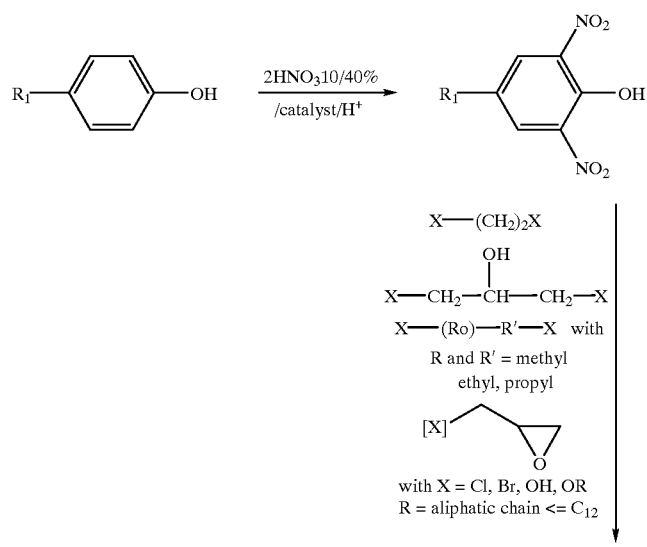

-continued

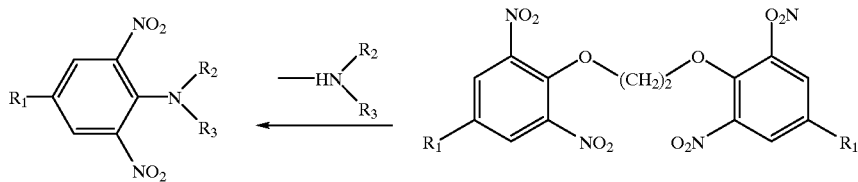

The invention will be easily understood from the following non-limitative examples, some of which relate to advantageous embodiments.

Examples 1 to 15 illustrate the dinitration stage of the 4-substituted phenol.

EXAMPLE 1

This is a comparative example in which dinitration is carried out without catalyst.

Within the space of 45 minutes and maintaining the temperature at 20–25° C., a solution of 6.5 g (43.0 mmol) of 4-tert-butyl-phenol in 26 g of methylene chloride is introduced into a nitrating medium constituted by a mixture of 17 g (108 mmol) of 40% nitric acid and 12 g of methylene chloride.

The medium contains 108 mmol, namely 2.4 equivalents of protons relative to the phenol.

The excess of nitrating agent is 25%.

This is left to react for one hour at 20–35° C., then for another hour at 40° C.

The organic phase is separated from the aqueous phase by decanting.

The aqueous phase is back-extracted with 12.17 g of methylene chloride.

The organic phases are combined, dried over $MgSO_4$, then concentrated to dryness using a device known by the name "ROTAVAPOR".

9.2 g of a yellowish brown solid is collected, constituted by:
72% of 2,6-dinitro-4-tert-butyl-phenol,
22% of 2-nitro-4-tert-butyl-phenol,
3.5% of 2,4-dinitrophenol and
2.3% of 4-nitrophenol.

The yield of sought product, i.e. 2,6-dinitro-4-tert-butyl-phenol, is 64.2%, and so is mediocre.

EXAMPLE 2

Within the space of 10 minutes and maintaining the temperature at 50° C., a solution of 4.5 g (30 mmol) of 4-tert-butyl-phenol in 45 g of 1,2-dichloroethane is introduced into a nitrating reaction mixture constituted by 6.1 g (71 mmol) of sodium nitrate dissolved in 32.2 g of 22% hydrochloric acid; this nitrating medium contains 83 mg of zinc chloride.

The excess of nitrating agent is 20%.

The quantity of protons present in the medium is 189 mmol, i.e. 6.3 equivalents relative to the phenol.

This is left to react for one hour at 50–55° C., and is then left to settle. The aqueous phase is back-extracted with 89 g of dichloroethane, then the combined organic phases are washed with 50 g of water.

Drying over magnesium sulphate is followed by evaporation of the solvent.

6.88 g of a compound is obtained, constituted by:
94.1% of 2,6-dinitro-4-tert-butyl-phenol,
0.7% of 2-nitro-4-tert-butyl-phenol and
3% of 2,4-dinitrophenol,
and accordingly the yield of the sought product is 95%.

EXAMPLE 3

Within the space of 5 minutes and maintaining the temperature at 50° C., a solution of 4.5 g (30 mmol) of 4-tert-butyl-phenol in 40 g of 1,2-dichloroethane is introduced into a nitrating reaction mixture constituted by 6.1 g (71 mmol) of sodium nitrate dissolved in 22.7 g of 17% HCl; this nitrating medium contains 64 mg of zincic chloride.

The excess of nitrating agent is 20%.

The quantity of protons present in the medium is 103 mmol, i.e. 3.4 equivalents relative to the phenol.

It is left to react for 30 minutes at 50° C., then the medium is maintained at 55° C. for 3 hours 30 minutes.

The phases are separated by decanting, the aqueous phase is back-extracted with 40 g of dichloroethane, the organic phases are combined and they are then washed with 20 g of water; they are then dried and the solvent is eliminated by evaporation.

7.1 g of a product is obtained containing 95.1% of 2,6-dinitro-4-tert-butyl-phenol, in which no mononitrated compound is found.

The yield of the sought dinitrated product is 93.8%.

EXAMPLE 4

Within the space of 30 minutes and maintaining the temperature at 50° C., a solution of 4.5 g (30 mmol) of 4-tert-butyl-phenol in 40 g of 1,2-dichloroethane is introduced into a nitrating reaction mixture constituted by 22.6 g of 20% nitric acid (72 mmol) and 1.5 g of 37% hydrochloric acid (15.2 mmol); the nitrating medium contains 122 mg of ferric chloride hexahydrate.

The excess of nitrating agent is 20%.

The medium contains a quantity of protons corresponding to 87.2 mmol, i.e. 2.9 equivalents relative to the phenol.

It is left to react for 4 hours at 55° C., then for 1 hour 30 minutes at 60° C.

The phases are separated by decanting and the aqueous phase is back-extracted with twice 20 g of 1,2-dichloroethane.

The organic phases are combined and then washed with 20 g of distilled water; these phases are then dried by evaporation.

7.01 g of a yellow solid product is obtained containing 96.5% of 2,6-dinitro-4-tert-butyl-phenol.

The yield of the sought dinitrated product is 94%.

EXAMPLE 5

Within the space of 30 minutes and maintaining the temperature at 50° C., a solution of 4.5 g (30 mmol) of 4-tert-butyl-phenol in 40 g of dichloroethane is introduced into a nitrating reaction mixture constituted by 23.5 g of 19.4% nitric acid (72 mmol) containing 120 mg of ferric chloride hexahydrate.

The excess of nitrating agent is 20%.

There are no other protons than those supplied by the nitric acid, i.e. 72 mmol and therefore 2.4 equivalents relative to the phenol.

It is left to react for 3 hours 30 minutes at 55° C., then the temperature is maintained at 60° C. for 1 hour.

The phases are separated by decanting, then the aqueous phase is back-extracted with 40 g of dichloroethane.

The organic phases are combined and are washed with 20 g of distilled water; they are dried and then the solvent is evaporated off.

7.00 g of a yellow solid is collected containing 90% of 2,6-dinitro-4-tert-butyl-phenol and 7.2% of 2-nitro-4-tert-butyl-phenol.

The yield of the sought dinitrated product is 87.5%.

This example shows than in the presence of an insufficient quantity of protons, dinitration stops at inadequate degrees of conversion.

EXAMPLE 6

This example shows that the minimum quantity of protons required can be supplied by an excess of nitric acid, which therefore acts as a co-acid in addition to its nitrating role.

Within the space of 30 minutes and maintaining the temperature at 50° C., a solution of 4.5 g (30 mmol) of 4-tert-butyl-phenol in 40 g of 1,2-dichloroethane is introduced into a reaction mixture constituted by 29.9 g of 18.5% nitric acid (i.e. 87.7 mmol), which corresponds to the total of 72 mmol of nitrating agent and 15.2 mmol of co-acid in Example 4; 120 mg of ferric chloride hexahydrate is added.

The excess of nitrating agent is 45%.

The proportion of protons is 2.9 equivalents.

It is left to react for 2 hours at a temperature of 55° C. The phases are separated by decanting.

The aqueous phase is separated and is extracted with twice 20 g of 1,2-dichloroethane.

The organic phases are combined, washed with 20 g of distilled water and dried by evaporation.

7.09 g of an orange solid is collected, constituted by
93.2% of 2,6-dinitro-4-tert-butyl-phenol and
7.1% of 2-nitro-4-tert-butyl-phenol.
The yield of the sought dinitrated product is 92%.

EXAMPLE 7

This example illustrates the possibility of recycling the nitric effluents collected at the end of a given dinitration stage, to a subsequent dinitration stage.

Within the space of 30 minutes and maintaining the temperature at 50° C., a solution of 9.0 g (60 mmol) of 4-tert-butyl-phenol in 80 g of 1,2-dichloroethane is introduced into a nitrating reaction mixture constituted by 32.5 g of 28% nitric acid (144 mmol) and 8.9 g of 37% hydrochloric acid (90 mmol); in addition this nitrating medium contains 310 mg of ferric chloride hexahydrate.

The excess of nitrating agent is 20%.

The proportion of protons is 3.9 equivalents.

It is left to react for 2 hours at a temperature of 55° C. The phases are separated by decanting; the aqueous phase is extracted with 40 g of dichloroethane.

34.6 g of nitric effluent is recovered, constituted by an aqueous phase containing:
3.1 g of hydrochloric acid and
1.44 g of nitric acid.

The organic phases are combined, dried over magnesium sulphate and evaporated to dryness.

14.18 g of a yellow-orange solid is collected, containing 95.1% of 2,6-dinitro-4-tert-butyl-phenol, which corresponds to a yield of 93.6%.

A new nitrating reaction mixture is established starting from 20 g of the nitric effluent recovered above; this nitric effluent contains 13.3 mmol of $HNO_3$ and 49.9 mmol of HCl and it is reconcentrated by the addition of 3.71 g of 99% nitric acid (58.3 mmol) and 0.5 g of 37% hydrochloric acid (5.1 mmol).

A solution of 4.5 g (30 mmol) of 4-tert-butyl-phenol in 40 g of 1,2-dichloroethane is introduced into this new nitrating medium within the space of 30 minutes and at a temperature of 50° C.

The excess of nitrating agent is 20%.

The proportion of protons is 4.2 equivalents.

It is left to react for 2 hours at 55° C.

After settling, the aqueous phase is separated and is extracted with 40 g of 1,2-dichloroethane.

The organic phases are combined, washed with 15 g of distilled water, then dried over magnesium sulphate before being evaporated to dryness.

7.1 g of a yellow-orange solid is collected containing 96.4% of 2,6-dinitro-4-tert-butyl-phenol.

The yield of dinitrated derivative is 95.1%.

EXAMPLE 8

This example illustrates the O-alkylation stage of the 4-substituted dinitrophenol.

A 50 ml flask equipped with a stirrer, condenser and thermometer is loaded with 2.5 g of tetrabutyl-ammonium 2,6-dinitro-4-tert-butyl-phenolate obtained by salification of 2,6-dinitro-4-tert-butyl-phenol, then 50 g of 2-bromopropane.

The reaction medium is heated to 60±2° C. for 6 hours.

The progress of reaction is monitored by thin-layer chromatography.

Then the reaction medium is cooled down to 25° C., and 30 g of 1,2-dichloroethane is added.

The reaction medium is washed twice with 30 g of 0.1N HCl.

The organic phase, separated after decanting, is washed twice with 10 g of 0.1M soda, then with 30 g of distilled water.

The organic phase is then dried over magnesium sulphate, then evaporated under vacuum.

1.27 g of a yellow-orange solid is collected constituted by 99.9% of 2-(2,6-dinitro-4-tert-butyl-phenoxy)propane, obtained with a yield of 86.7%.

The mother aqueous phases and those from washing are back-extracted at pH 1 with 100 g of 1,2-dichloroethane.

After drying and evaporation of the solvent, 0.15 g of an orange solid is collected constituted by 95% of unreacted 2,6-dinitro-4-tert-butyl-phenol which can be recycled to another O-alkylation operation.

EXAMPLE 9

This example illustrates the amination stage.

A 25 ml three-necked flask equipped with a stirrer, a condenser and a thermometer is loaded with 1 g of 2-(2,6- dinitro-4-tert-butyl-phenoxy)propane with a purity of 99%, 5.2 g of amino-2-butane and 8 g of isopropanol.

It is left to react at 45° C. for 2 hours, then at 60° C. for 7 hours.

Using thin-layer chromatography of an aliquot of reaction medium, the end of reaction is detected by the disappearance of the ether.

The solvent and the excess of amine are evaporated off under vacuum; the residue obtained is taken up in dichloromethane and then washed with 15 g of 0.1N HCl, then with 15 g of 0.1M soda, and then with 20 g of water until neutrality is achieved; then it is dried and evaporated to dryness under vacuum.

1.02 g of an orange-yellow solid is obtained constituted by 99.1% (by GC) of 4-tert-butyl-N(sec-butyl)-2,6-dinitro-benzene-amine, which corresponds to a yield of 97.5%.

EXAMPLE 10

This example illustrates the preparations of 3-(2,6-dinitro-4-tert-butyl-phenoxy)-1,2-oxopropane and of hydroxy-poly (2-ol-propanoxy)-2,6-dinitro-4-tert-butyl-benzene.

A 100 ml three-necked flask equipped with a stirrer, a condenser and a thermometer is loaded with 3.85 g (8 mmol) of tetrabutylammonium 2,6-dinitro-4-tert-butyl-phenate obtained by salification of 2,6-dinitro-4-tert-butyl-phenol, then 25 g of toluene; then 11 g (82 mmol) of epibromohydrin is added over 6 hours at 100° C.

The progress of reaction is monitored by thin-layer chromatography.

The reaction medium is cooled down to 25° C., the aqueous phase is washed with 10 g of toluene at pH 7, the toluene phases are combined and are then evaporated to dryness.

3.6 g of crude polyether is collected, and it is used as it is in the amination stage.

EXAMPLE 11

This example illustrates the formation of butralin starting from hydroxy-poly(2-ol-propanoxy)-2,6-dinitro-4-tert-butyl-benzene.

A 50 ml three-necked flask equipped with a stirrer, a condenser and a thermometer is loaded with 2.8 g of the raw polyether constituted by the hydroxypoly (2-ol-propanoxy) -2,6-dinitro-4-tert-butyl-benzene prepared in example 10, then 18.3 g (250 mmol) of amino-2-butane; the temperature is raised to 65° C. and is kept at that level for 5 hours.

The progress of reaction is monitored by thin-layer chromatography.

The excess of amino-2-butane is distilled under vacuum, cooled down to 55° C., 30 g of xylene and 15 g of water are added; the aqueous phase is washed with 10 g of toluene, the toluene organic phases are combined and evaporated to dryness.

2.5 g of a gummy solid is collected, which is recrystallized from 5.5 g of isopropanol.

1.82 g of a solid is obtained constituted by 82.5% (GC) of 4-tert-butyl-N(sec-butyl)-2,6-dinitro-benzene-amine.

Separative chromatography of the product at 82.5% leads to isolation of a butralin with a purity of 98%.

EXAMPLE 12

This example illustrates the O-alkylation stage by an oxirane of a 4-substituted dinitrophenol.

10 g of 2,6-dinitro-4-tertbutylphenol, 7.6 g of xylene and 0.04 g of pyridine are loaded into a 100 ml reaction vessel equipped with magnetic stirring, a manometer and a bursting disk (40 bars). The reaction medium is cooled down to 10° C. and 3 g of propylene oxide is poured in. The reaction vessel is closed and subjected to a nitrogen pressure of 2–3 bars.

The reaction medium is heated at 120° C. for 3 hours.

After cooling down to 30° C., decompression is carried out.

After the xylene has been evaporated off, 12.8 g of a brown solid is collected composed of 93.61% of 2-propanol-1-(2,6-dinitro-4-tertbutylphenoxy) and 4.1% of (2,6-dinitro-3,4-tertbutylphenoxy)-propanoxy-propanol.

EXAMPLE 13

This example illustrates the O-alkylation stage by an oxirane of a 4-substituted dinitrophenol.

35 g of 2,6-dinitro-4-tertbutylphenol, 35 g of xylene and 0.11 g of pyridine are loaded into a 100 ml reaction vessel equipped with magnetic stirring, a manometer and a bursting disk (40 bars). The reaction medium is cooled down to 10° C. and 8.5 g of ethylene oxide is poured in. The reaction vessel is closed and subjected to a nitrogen pressure of 2–3 bars.

The reaction medium is heated at 130° C. for 5 hours.

After cooling down to 30° C., decompression is carried out.

After the xylene has been evaporated off, 41.46 g of an orange solid is collected composed of 92.65% of ethanol-2-(2,6-dinitro-4-tertbutylphenoxy) and of 3.01% of (2,6-dinitro-4-tertbutylphenoxy)-ethoxy-ethanol.

EXAMPLE 14

This example illustrates the amination stage of 1-(2,6-dinitro-4-tertbutylphenoxy)2-propanol.

11.3 g of 2-propanol-1-(2,6-dinitro-4-tertbutyl-phenoxy) of 95.93% purity and of 1.94% of the diaddition product, 3.8 g of amino-2-butane, 0.3 g of $CaCl_2$, $6H_2O$ and 34.2 g of xylene are loaded into a 50 ml three-necked flask equipped with a magnetic stirrer, a condenser (−10° C.) and a thermometer.

The mixture is maintained under reflux (50° C.) for 8 hours.

Using thin-layer chromatography on an aliquot of the reaction medium, the end of the reaction is detected by the disappearance of the ether.

The solvent and the excess of amine are then evaporated under vacuum.

The residue obtained is taken up in dichloromethane, then washed with 50 g of water. It is then evaporated under vacuum.

10.2 g of an orange solid is obtained constituted by 95.3% (determined by gas chromatography) of N-(1-methylpropyl)-2,6-dinitro-4-tertbutyl-benzen-amine.

EXAMPLE 15

This example illustrates the amination stage of 1-(2,6-dinitro-4-tertbutylphenoxy)2-ethanol.

33.0 g of ethanol-2-(2,6-dinitro-4-tertbutyl-phenoxy) of 95.0% purity and of 3.24% of (2,6-dinitro-4-tertbutylphenoxy) ethoxy-ethanol, 9.93 g of amino-3-butane and 0.7 g of $CaCl_2$, $6H_2O$ are loaded into a 50 ml three-necked flask equipped with a magnetic stirrer, a condenser (−10° C.) and a thermometer.

The mixture is maintained under reflux (65° C.) for 2 hours.

By using thin-layer chromatography on an aliquot of the reaction medium, the end of the reaction is detected by the disappearance of the ether.

The solvent and the excess of amine are then evaporated under vacuum.

The residue obtained is taken up in cyclohexane, then washed with 25 g of water. It is then evaporated under vacuum.

31.84 g of an orange solid is obtained constituted by 96.6% (determined by gas chromatography) of N-(1-methylpropyl)-2,6-dinitro-4-tertbutyl-benzen-amine.

We claim:

1. Process for the preparation of 4-substituted dinitroanilines of formula

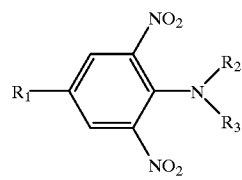

(I)

in which
R$_1$ represents a radical selected from the group consisting of tert-butyl, sulphonamido, trifluoro-methyl, methylsulphonyl and isopropyl,
R$_2$ and R$_3$, which are identical or different from one another, are selected from the group consisting of hydrogen atom, and of the linear and branched alkyl, cycloalkyl, haloalkyl and alkenyl radicals containing less than 6 carbon atoms, said process comprising successively:
selecting the 4-substituted phenol corresponding to the contemplated 4-substituted dinitro-aniline,
dinitrating the said 4-substituted phenol in a reaction medium containing a slight excess of nitrating agent, a quantity of protons from 2 to 7 equivalents with respect to the phenol and a catalyst selected from the group consisting of the soluble salts of the transition metals of columns IV to XII of the Periodic Table,
O-alkylating the thus obtained dinitrated 4-substituted phenol by means of an alkylating agent selected from the group consisting of linear and branched alkyl mono-halides having at least 3 carbon atoms, of linear and branched alkyl polyhalides having at least 2 carbon atoms, of polyalkoxy-haloalkyl ethers represented by the formula (RO)$_n$R'X in which X represents a hydrogen atom, chlorine, bromine or iodine atom and in which R and R', independently of one another, represent a methyl, ethyl or propyl radical, n being such that the number of carbon atoms in the alkylating agent is $\geq 2$, of the ethylene oxide and of the propylene oxide and of compounds whose structure corresponds to the formula

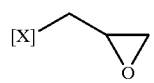

which represents epihalohydrins when X represents Cl or Br, glycidol when X represents OH, glycidyl ethers when X represents OR, R being an aliphatic chain with at most 12 carbon atoms, and oxirane when X is an aliphatic chain R with 1 to 12 carbon atoms,
aminating the thus obtained 4-substituted dinitrated phenoxy-ether by using a primary or a secondary amine.

2. Process according to claim 1, wherein the catalyst is selected from the group consisting of the soluble salts of Fe$_{III}$, Fe$_{II}$, Zn$_{II}$ and Cu$_{II}$ ions.

3. Process according to claim 1, wherein the linear and branched alkyl monohalides having at least 3 carbon atoms as well as the linear and branched alkyl polyhalides having at least 2 carbon atoms contain a saturated ring or at least one unsaturation and wherein the polyalkoxy-haloalkyl ethers of formula (RO)$_n$R'X are selected from the group consisting of the chloromethyl-polymethoxy ethers and the chloromethyl-polyethoxy ethers.

4. Process according to claim 1, wherein the proportion of catalyst relative to the phenol is from 1 to 50 per thousand.

5. Process according to claim 4, wherein the proportion of catalyst relative to the phenol is from 5 to 30 per thousand.

6. Process according to claim 1, wherein the quantity of protons present in the nitrating medium is from 2.4 to 6 equivalents with respect to the phenol.

7. Process according to claim 6, wherein the quantity of protons present in the nitrating medium is from 2.6 to 2.9 equivalents with respect to the phenol.

8. Process according to claim 7, wherein the protons present in the nitrating medium are provided by an inorganic or by an organic acid called co-acid and selected from the group consisting of the hydrochloric, the hydrobromic, the sulphuric, the phosphoric acids and the lower carboxylic acids.

9. Process according to claim 8, wherein the lower carboxylic acid is selected from the group consisting of the acetic, the propionic and the oxalic acid.

10. Process according to claim 1, wherein the alkylating agent used during the O-alkylation stage is selected from the group consisting of the alkyl monohalides represented by the formula C$_n$H$_{2n-1}$X in which X is a chlorine, bromine or iodine atom and n is $\geq 3$, and of the alkyl polyhalides represented by the formula C$_n$H$_{2n-m}$X$_{2+m}$ in which X is an atom of chlorine, bromine or iodine and n$\geq 2$ with $0 \leq m \geq 2n$.

11. Process according to claim 10, wherein the alkylating agent is selected from the group consisting of, as alkyl monohalides, the n-propyl, isopropyl, n-butyl, sec-butyl, isobutyl, tert-butyl, n-pentyl, sec-amyl, 3-pentyl, neopentyl, hexyl, isohexyl, cyclohexyl, cyclopropyl, benzyl, allyl and polyalkoxyalkyl halides, with a methoxy, ethoxy or propanoxy radical as alkoxylated chain and, as alkyl polyhalides, the dichloroethane, the dibromoethane, the 1,2- and the 1,3-dichloro-propane.

12. Process according to claim 1, wherein the amination stage is carried out in an inert solvent selected from the group consisting of the aromatic solvents and alcohols by reacting, at atmospheric pressure or under 3 to 5 atmospheres and at a temperature between 30° C. and the reflux temperature of the medium, the O-alkylated dinitrated 4-substituted phenol with an excess of a secondary or primary amine selected from the group consisting of amino-2-butane, N,N-diethylamine, N,N-dipropylamine, N-ethyl, N-butylamine, N-propyl,N-methyl-cyclopropylamine, N-(2-chloroethyl),N-propylamine, N-propyl, N-2-methyl-2-propenyl-amine, N-ethyl-,N-2-methyl-2-propenyl-amine.

* * * * *